US009327104B2

(12) United States Patent
Morriss et al.

(10) Patent No.: US 9,327,104 B2
(45) Date of Patent: May 3, 2016

(54) METHODS AND APPARATUS FOR DELIVERING A THERAPEUTIC AGENT TO NASOPHARYNGEAL MUCOSA TARGETS

(71) Applicant: The Foundry, LLC, Menlo Park, CA (US)

(72) Inventors: John Morriss, San Francisco, CA (US); Cary Reich, Los Gatos, CA (US); Hanson Gifford, Woodside, CA (US)

(73) Assignee: The Foundry, LLC, Menlo Park, CA (US)

( * ) Notice: Subject to any disclaimer, the term of this patent is extended or adjusted under 35 U.S.C. 154(b) by 0 days.

(21) Appl. No.: 14/151,767

(22) Filed: Jan. 9, 2014

(65) Prior Publication Data

US 2014/0242064 A1 Aug. 28, 2014

Related U.S. Application Data

(63) Continuation of application No. PCT/US2012/046089, filed on Jul. 10, 2012.

(60) Provisional application No. 61/507,417, filed on Jul. 13, 2011.

(51) Int. Cl.

*A61M 31/00* (2006.01)
*A61K 9/00* (2006.01)
*A61K 9/12* (2006.01)

(52) U.S. Cl.

CPC .............. *A61M 31/00* (2013.01); *A61K 9/0043* (2013.01); *A61K 9/122* (2013.01)

(58) Field of Classification Search

CPC .................................................... A61K 9/0043
See application file for complete search history.

(56) References Cited

U.S. PATENT DOCUMENTS 3,471,064 A 10/1969 Micallef
4,207,891 A 6/1980 Bolduc
5,336,163 A * 8/1994 DeMane et al. ................ 602/46
5,662,929 A 9/1997 Lagace et al.
5,766,605 A 6/1998 Sanders et al.
5,791,337 A 8/1998 Coles et al.
6,974,578 B1 12/2005 Aoki et al.
7,655,243 B2 2/2010 Deem et al.
2004/0197270 A1 10/2004 Mundschenk
2005/0072430 A1 4/2005 Djupesland
2005/0281751 A1 12/2005 Levin
2007/0267011 A1 11/2007 Deem et al.
2008/0216838 A1 9/2008 Wondka
2010/0121308 A1 5/2010 Muni et al.
2011/0044903 A1 * 2/2011 Borrelli .......................... 424/9.1

FOREIGN PATENT DOCUMENTS

CN 101027042 A 8/2007
WO WO 2004/048519 A2 6/2004
WO WO 2006/036417 A1 4/2006
WO WO 2009/158687 A1 12/2009
WO WO 2011/039637 A2 4/2011
WO WO 2011/049960 A2 4/2011

OTHER PUBLICATIONS

Auerbach, “Nosebleed”, Web post, 2009, 1 page.*
Ozcan et al. “The effect of intranasal injection of botulinum toxin A on the symptoms of vasomotor rhinitis”, American J of Otolaryngology-Head and Neck Medicine and Surgery, 2006, 27:314-318.*
Joseph “Understanding foams & foaming”, J of Fluids Engineering, 1997, p. 1-8.*
International search report and written opinion dated Nov. 9, 2012 for PCT/US2012/046089.
Shaari, et al. Rhinorrhea is decreased in dogs after nasal application of botulinum toxin. Otolaryngol Head Neck Surg. Apr. 1995;112(4):566-71.
Unal, et al. Effect of botulinum toxin type A on nasal symptoms in patients with allergic rhinitis: a double-blind, placebo-controlled clinical trial. Acta Otolaryngol. Dec. 2003;123(9):1060-3.
European search report and search opinion dated Dec. 12, 2014 for EP Application No. 12811983.1.

* cited by examiner

*Primary Examiner* — Bin Shen

(74) *Attorney, Agent, or Firm* — Wilson, Sonsini, Goodrich & Rosati

(57) ABSTRACT

A system for delivering a therapeutic agent to a nasopharyngeal mucosa target comprises a foam generating mechanism, a gas, a therapeutic agent in liquid form that inhibits mucus production, and a delivery device. Actuation of the foam generating mechanism entraps gaseous bubbles from the gas in the liquid thereby forming a foam. The therapeutic agent is dispersed in the foam which has an expanded configuration adapted to fill a nasopharyngeal space and deliver the therapeutic agent to the mucosa targets. The delivery device is for delivering the foam to the nasopharyngeal space. The foam may also have a collapsed configuration for removal from the nasopharyngeal space or for concentration of the therapeutic agent onto the mucosa.

24 Claims, 7 Drawing Sheets

METHODS AND APPARATUS FOR DELIVERING A THERAPEUTIC AGENT TO NASOPHARYNGEAL MUCOSA TARGETS

CROSS-REFERENCES TO RELATED APPLICATIONS

The present application is a continuation of International PCT Application No. PCT/US2012/046089, filed Jul. 10, 2012, which is a PCT of and claims the benefit of U.S. Provisional Patent Application No. 61/507,417 filed Jul. 13, 2011; the entire contents of which are incorporated herein by reference.

This application is related to U.S. patent application Ser. No. 11/750,967 filed May 18, 2008, the entire contents of which are incorporated herein by reference. This application is also related to U.S. Provisional Patent Application No. 61/507,422 filed Jul. 13, 2011; the entire contents of each of which are incorporated herein by reference.

BACKGROUND OF THE INVENTION

1. Field of the Invention

The present disclosure relates generally to medical methods and delivery systems. More particularly, the present disclosure relates to methods and systems for delivering therapeutic agents such as toxins to mucosa targets in a nasopharyngeal space. The present disclosure also relates to delivery of other therapeutic agents including non-toxin based agents. While the present disclosure is focused on the treatment of rhinitis, this is only an exemplary embodiment and is not intended to be limiting Rhinitis is commonly referred to as “stuffy nose,” and results from inflammation and swelling of the mucus membranes lining the nasal cavity Rhinitis falls into two major categories—allergic and non-allergic (or vasomotor). Chronic rhinitis can result in chronic inflammation of the nasal passages resulting in sinusitis, an infection or inflammation of the paranasal sinuses. Rhinitis includes the symptoms of rhinorrhea which is commonly referred to as “runny nose.” Rhinorrhea describes the effluence of mucus from the lining of the nasal passages, nasopharynx, or paranasal sinuses. Rhinorrhea can be a symptom of a number of diseases such as the common cold, or sinusitis.

Allergic rhinitis is an immunologic response modulated by immunoglobulin E (IgE) and characterized predominantly by sneezing, rhinorrhea, nasal congestion, and pruritus of the nose. It may be seasonal (a condition commonly referred to as hay fever) or perennial. The seasonal form is caused by allergens released during tree, grass, or weed pollination, whereas the perennial form is caused by allergies to animal dander, dust mites, or mold spores with or without associated pollinosis. Data also suggest that urban air pollutants from automobiles and other sources may have an adjunctive effect.

Non-allergic rhinitis may be caused by anatomic pathologies such as blockages, as seen in the case of sinusitis. Symptoms may include sneezing, itching, nasal congestion, and a runny nose. Non-allergic rhinitis is a diagnosis of rhinitis without any IgE mediation, as documented by allergen skin testing. Hence, the rhinorrhea, sneezing, pruritus, and congestion do not result from allergy or hypersensitivity and continue to persist, whether continuously or sporadically. Non-allergic rhinitis affects 5-10% of the population. Non-allergic rhinitis has 7 basic subclassifications, including infectious rhinitis, non-allergic rhinitis with eosinophilia syndrome (NARES), occupational rhinitis, hormonal rhinitis, drug-induced rhinitis, gustatory rhinitis, and vasomotor rhinitis. Patients may or may not present with the same symptoms seen in allergic rhinitis.

While numerous treatments for rhinitis have been proposed over the years, no single treatment is optimum for all patients or all conditions. Most commonly, hay fever and other forms of rhinitis are treated with antihistamines which block the inflammatory response. While effective, many antihistamines are also undesirable because they can cause drowsiness, or they may have a limited duration of effect, and they can present the patient with an on-going cost associated with continuous purchase of the drugs.

Recently, a longer term therapy for rhinitis which relies on the use of botulinum toxin (BoNT) for blocking mucus production by mucus-producing cells in the nasal membrane has been proposed. Botulinum toxin and other neurotoxins are capable of disabling adrenergic cells, including epithelial or goblet cells which are responsible for the majority of mucus production in the nasal cavity membrane. It has been published in the scientific literature that introduction of botulinum toxin into the nasal passages of canines can reduce mucus secretion by a significant amount. This work is further discussed in scientific and patent publications by U.S. Pat. No. 5,766,605 to Sanders, as well as by U.S. Pat. No. 7,655,243 to Deem et al.

While the use of botulinum toxin appears to hold promise for long term rhinitis treatment, it faces a number of challenges before it is suitable for widespread use in humans. In particular, botulinum toxin is a neurotoxin which could have significant negative effects on a patient if accidentally released outside of the targeted nasal passages. Inadvertent distribution of the toxin to muscles of the oropharynx, mouth, tongue, or elsewhere could result in serious complications to the patient. Additionally, the use of botulinum-soaked gauze pads for delivering the toxin to the nasal cavities, as reported in the scientific literature, will have limited ability to uniformly and selectively deliver the botulinum to the regions having high concentrations of preferred target cells, such as epithelial or goblet cells in the nasopharynx. Moreover, gauze pads or weeping balloons that are used to deliver a toxin may apply a very low concentration of the toxin to the target tissue, or they will contain a total dose of toxin which could be harmful or fatal if improperly delivered. It would be desirable therefore to provide devices and methods that deliver a high concentration of toxin to the target tissue while maintaining the total toxin volume at a safe level.

For these reasons, it would be desirable to provide improved methods and systems for delivering the correct dose of toxin in a controlled manner to a target treatment site. Such improved methods and systems are preferably used to deliver a toxin, such as botulinum toxin to the nasal membrane of a patient, particularly in a patient suffering from rhinitis or other conditions associated with nasal inflammation and conditions, such as sinus headaches and migraine headaches. The methods and systems should be capable of providing for selective and repeatable delivery of an appropriate dose of the toxins to a defined target areas within the nasal cavities, including particular paranasal sinuses, the nasopharynx, and in some cases substantially the entire nasal cavity. The systems and methods should provide for the safe, accurate and effective delivery of a proper dose of the toxins, and in particular should reduce or eliminate the risk of toxin being delivered to non-targeted tissues outside of the nasal cavity. At least some of these objectives will be met by the inventions described herein below.

2. Description of the Background Art

Patents and publications related to delivery of a toxin to the nasal cavity include U.S. Pat. Nos. 5,766,605 and 6,974,578; and U.S. Patent Publication No. 2005/0281751. Related scientific literature includes Sharri et al. (1995) *Otolaryngol. Head Neck Surg.* 112: 566-571 which further discusses the work disclosed in U.S. Pat. No. 5,766,605. Ünal et al. (2002) *Acta Otolaryngol* 123: 1060-1063 describes the injection of botulinum toxin A into the turbinates of patients suffering from allergic rhinitis. The use of catheters and other devices for the energy-mediated delivery of botulinum light chain is described in commonly owned co-pending U.S. patent application Ser. No. 11/750,967, the entire contents of which are incorporated herein by reference.

BRIEF SUMMARY OF THE INVENTION

Briefly and in general terms, the present invention provides methods and systems for delivery of a therapeutic agent. The therapeutic agent may be a toxin or a non-toxin and in preferred embodiments is delivered to the nasal cavity. When toxins are used, the invention provides for the delivery of the toxin to and across the nasal membrane tissue to treat various conditions and symptoms associated with nasal inflammation, including, rhinorrhea, rhinitis, sinusitis and hay fever.

The region where the toxin is introduced may comprise any portion of the nasal cavity, such as the turbinates, a single paranasal sinus or portion thereof, a main nasal passage, two or more paranasal sinuses, or in some cases may comprise substantially the entire nasal cavity of the patient. A particular target region for the toxin may comprise the nasopharynx which is at the back of the nasal passage. The nasopharynx comprises a cluster of epithelial or goblet cells which are responsible for mucus secretion and which are susceptible to the disabling mechanism of the botulinum toxin and other neurotoxins.

The therapeutic agent to be delivered may be any agent that helps alleviate the symptoms of rhinitis. Preferred therapeutic agents include toxins, and the toxin may comprise any neurotoxin capable of disabling mucus secretion in epithelial or goblet cells and other mucus-producing nasal cells. Preferably, the toxin comprises botulinum toxin, although other toxins such as ricin, exotoxin A, diphtheria toxin, cholera toxin, tetanus toxin, other neurotoxins, and active fragments thereof may also find use.

In addition to the methods described above, the present invention further provides systems for delivering toxins to epithelial or goblet and other target cells as defined above in a nasal membrane.

In a first aspect of the present invention, a system for delivering a therapeutic agent to a nasopharyngeal mucosa target comprises a foam generating mechanism, a gas, a therapeutic agent in liquid form that is adapted to inhibit production of mucus, and a delivery device. Actuation of the foam generating mechanism entraps gaseous bubbles from the gas in the therapeutic agent thereby forming a foam. The therapeutic agent is dispersed in the foam which has an expanded configuration adapted to fill a nasopharyngeal space and deliver the therapeutic agent to the mucosa target. The delivery device delivers the foam to the nasopharyngeal space.

The foam generating mechanism may comprise a pump, or a pressurized container wherein the gas is entrapped in the liquid. The foam generating mechanism may also comprise a container holding the gas, the liquid, and the therapeutic agent. Agitation of the container or its contents mixes the contents therein and forms the foam. The foam generating mechanism may further comprise a second actuation mechanism for ejecting the foam therefrom.

The gas may comprise air, nitrous oxide or other gases. The system may further comprise a liquid which may be an aqueous solution such as saline or other liquids such as those described below. The therapeutic agent may comprise a non-toxin or a toxin configured to inhibit mucus secretions, such as botulinum toxin. The therapeutic agent may be mixed in the liquid.

The delivery device may comprise an elongate shaft coupled to the foam generating mechanism. The elongate shaft may be sized to fit into the nasopharyngeal space and may be configured to deliver the foam to the mucosa target. The delivery device may comprise a syringe.

The system may further comprise a surfactant mixed with the liquid. The surfactant may be adapted to lower surface tension of the liquid, thereby facilitating formation of the foam upon actuation of the foam generating mechanism. The surfactant may comprise at least one of soap, sodium dodecyl sulfate, and a polysorbate surfactant.

The system may further comprise an anti-foaming agent configured to break the foam down following delivery into the nasopharyngeal space to enable removal therefrom. The system may comprise an anti-foaming agent configured to break the foam down following delivery into the nasopharyngeal space so as to concentrate the therapeutic agent onto the mucosa. The anti-foaming agent may comprise one of simethicone, silicone oil, polyethylene glycol, polypropylene glycol copolymer, and detergent. The foam may be configured to remain in the expanded configuration for a time period long enough for an effective amount of the therapeutic agent to be absorbed by the mucosa target. The foam may have an expanded configuration for delivery into the nasopharyngeal space and a collapsed configuration for removal therefrom. The expanded configuration may have a volume at least ten times greater than the volume of the foam in the collapsed configuration. The foam may also have a collapsed configuration which applies a higher concentration and/or a smaller volume of the therapeutic agent or foam to the mucosa or target tissue. The system may further comprise an expandable member disposed adjacent a distal end of an elongate shaft. The expandable member may have a collapsed configuration and an expanded configuration, wherein the collapsed configuration may be adapted to be delivered and positioned in a body cavity, and wherein the expanded configuration may substantially fill the body cavity while maintaining a space between an outer surface of the expandable member and a wall of the body cavity.

In another aspect of the present invention, a system for delivering a therapeutic agent to a nasopharyngeal mucosa target comprises a slurry, a therapeutic agent dispersed in the slurry, and a delivery device for delivering the slurry and therapeutic agent to the mucosa target. The slurry comprises solid particles suspended in a liquid.

The solid particles may be porous, and the pores may be smaller than the molecule size of the therapeutic agent. The slurry may comprise a thickening agent selected from a gelatin, a thrombin, and a hemostatic agent configured to cause expansion of the slurry during contact with the mucosa target. The thickening agent may comprise at least one of thrombin, polyvinylpyrrolidone, oxidized cellulose polymer, collagen, porcine skin, gelatin, crosslinked gelatin, and porcine gelatin.

The liquid may comprise an aqueous solution such as saline. The therapeutic agent may comprise a toxin such as botulinum toxin that is configured to inhibit mucus secretions in the nasopharyngeal space. The delivery device may comprise a syringe or pump.

In yet another aspect of the present invention, a method for delivering a therapeutic agent to a nasopharyngeal mucosa target comprises entrapping gaseous bubbles in a liquid thereby forming a foam, and dispersing a therapeutic agent in at least one of the liquid or the foam. The method also includes the steps of delivering the foam to a nasopharyngeal space so that the therapeutic agent is delivered to the mucosa target, and removing the foam from the nasopharyngeal space.

Entrapping gaseous bubbles in the liquid may comprise actuating a foam generating mechanism. The foam generating mechanism may comprise a pump, or a pressurized container wherein the gas is passed into the liquid. The foam generating mechanism may comprise a container holding the gas, the liquid, and the therapeutic agent, and the method may further comprise agitating the container or its contents to mix the contents therein thereby forming the foam with the therapeutic agent dispersed therein. The gaseous bubbles may comprise air or nitrous oxide. The liquid may comprise an aqueous solution such as saline. Entrapping the gaseous bubbles may further comprise adding a surfactant to the liquid thereby lowering surface tension between the bubbles and the liquid so as to facilitate formation of the foam. The surfactant may comprise at least one of soap, sodium dodecyl sulfate, and a polysorbate surfactant.

The therapeutic agent may comprise a toxin such as botulinum toxin, configured to inhibit mucus secretions. Delivering the foam may comprise substantially filling up the nasopharyngeal space with the foam. Delivering the foam may also comprise advancing an elongate shaft into the nasopharyngeal space and passing the foam therethrough to the mucosa target. Delivering the foam may comprise passing the foam through a syringe. The method may further comprise retaining the foam in the nasopharyngeal space for a time period long enough for an effective amount of the therapeutic agent to be absorbed by the mucosa target. Delivering the foam may comprise actuating a pump mechanism.

The foam may be further optimized so that the bubbles dissolve fairly quickly and the foam breaks down into a thin coating on all of the mucous membranes. This coating may be further optimized to be sticky, keeping the coating with a relatively high concentration of therapeutic agent in contact with the mucous membranes for an extended period of time.

Removing the foam may comprise aspirating the foam from the nasopharyngeal space. Removing the foam may also comprise adding an anti-foaming agent to the foam thereby breaking the foam down into a reduced volume configuration for removal from the nasopharyngeal space. Removal of the foam may comprise expulsion from the nasopharyngeal space by nose blowing by the patient. The anti-foaming agent may comprise one of simethicone, silicone oil, polyethylene glycol, polypropylene glycol copolymer, and detergent. The therapeutic agent may alleviate symptoms associated with rhinhitis. The method may further comprise expanding an expandable member in the nasopharyngeal space while maintaining a space between an outer surface of the expandable member and a wall of the nasopharyngeal space. The foam may be delivered to the space between the outer surface of the expandable member and the wall of the nasopharyngeal space.

In still another aspect of the present invention, a method for delivering a therapeutic agent to a nasopharyngeal mucosa target comprises dispersing a therapeutic agent in a slurry that comprises solid particles dispersed in a liquid. The method also comprises delivering the slurry to a nasopharyngeal space so that the therapeutic agent is delivered to the mucosa target, and removing the slurry from the nasopharyngeal space.

The liquid may comprise an aqueous solution such as saline. The therapeutic agent may comprise a toxin such as botulinum toxin, and the toxin may inhibit mucus secretions in the nasopharyngeal space. Delivering the slurry may comprise passing the slurry through a syringe and substantially filling up the nasopharyngeal space with the slurry. The method may further comprise retaining the slurry in the nasopharyngeal space for a time period long enough for an effective amount of the therapeutic agent to be absorbed by the mucosa target. Removing the slurry may comprise aspirating the slurry from the nasopharyngeal space.

The method may further comprise expanding the slurry in the nasopharyngeal space so that the slurry contacts the mucosa target. The slurry may be expanded with a thickening agent selected from a gelatin, a thrombin, and a hemostatic agent. Other thickening agents may comprise at least one of thrombin, polyvinylpyrrolidone, oxidized cellulose polymer, collagen, porcine skin, gelatin, cross linked gelatin, and porcine gelatin. The therapeutic agent may alleviate symptoms associated with rhinitis.

In still another aspect of the present invention, a method for delivering a therapeutic agent to a nasopharyngeal mucosa target comprises delivering a therapeutic agent to a nasopharyngeal space in a first state suitable for delivery into a mucosa target, changing the state of the agent to a form suitable for removal from the nasopharyngeal space, and removing the therapeutic agent from the nasopharyngeal space.

Delivering the therapeutic agent in the first state may comprise delivering the therapeutic agent in a foam configuration. Changing the state of the agent may comprise changing the agent from a foam configuration to a liquid configuration. Changing the state may comprise adding an anti-foaming agent to the foam. Removing the therapeutic agent may comprise aspirating the therapeutic agent from the nasopharyngeal space. The therapeutic agent may comprise a toxin adapted to inhibit mucus secretions. The toxin may comprise botulinum toxin.

In another aspect of the present invention, a method of delivering a therapeutic agent to a body cavity comprises entrapping gaseous bubbles in a liquid thereby forming a foam, dispersing a therapeutic agent in at least one of the liquid or the foam, delivering the foam to the body cavity so that the therapeutic agent is delivered to target tissue in the body cavity, and removing the foam from the body cavity.

Entrapping gaseous bubbles in the liquid may comprise actuating a foam generating mechanism such as a pump. The gaseous bubbles may comprise air, and the liquid may comprise an aqueous solution such as saline. Entrapping the gaseous bubbles may further comprise adding a surfactant to the liquid thereby lowering surface tension of the liquid so as to facilitate formation of the foam. The surfactant may comprise at least one of soap, sodium dodecyl sulfate, and a polysorbate surfactant.

The therapeutic agent may comprise a toxin such as botulinum toxin that is configured to inhibit mucus secretions. Delivering the foam may comprise substantially filling up the body cavity with the foam. Delivering the foam may also comprise advancing an elongate shaft into the body cavity and passing the foam therethrough to the target tissue. The body cavity may comprise a vagina, and advancing the elongate shaft may comprise advancing the elongate shaft into the vagina. The body cavity may comprise a bladder, and advancing the elongate shaft may comprise advancing the elongate shaft through the urethra into the bladder. The body cavity may comprise the rectum, and advancing the elongate shaft may comprise advancing the elongate shaft through the anus. The body cavity may comprise the ear, and advancing the elongate shaft may comprise advancing the elongate shaft through the ear canal.

The foam may be retained in the body cavity for a time period long enough for an effective amount of the therapeutic agent to be absorbed by the target tissue. Delivering the foam may comprise actuating a pump mechanism. Removing the foam may comprise aspirating the foam from the body cavity. Removing the foam may also comprise adding an anti-foaming agent to the foam thereby breaking the foam down into a reduced volume configuration for removal from the nasopharyngeal space.

These and other embodiments are described in further detail in the following description related to the appended drawing figures.

DETAILED DESCRIPTION OF THE INVENTION

The present invention is preferably directed to methods and systems for delivering therapeutic agents such as toxins or non-toxins to target cells within a patient's nasal cavity. The toxins may be intact toxins, such as botulinum toxin, ricin, exotoxin A, diphtheria toxin, cholera toxin, tetanus toxin, other neurotoxins, and active fragments thereof. Each of these toxins comprises a heavy chain responsible for cell binding and a light chain having enzyme activity responsible for cell toxicity.

Botulinum toxin blocks acetylcholine release from cells, such as the epithelial or goblet cells in the nasal membranes responsible for mucus hypersecretion, and can thus be effective in accordance with the principles of the present invention. The use of energy to permeabilize or porate the cell membranes of the epithelial or goblet cells or other mucus-secreting cells of the nasal lining, may facilitate botulinum and other toxins to be preferentially delivered to the targeted epithelial or goblet and other mucus-producing cells. Additionally, energy-mediation allows use of the active or light chains of these toxins (having the heavy chains removed or inactivated) for treatments. Normally, the light chains when separated from the cell-binding heavy chains of botulinum and the other toxins are incapable of entering the cells and thus will be free from significant cell toxicity. By using energy-mediated protocols the toxin light chains may be locally and specifically introduced into the target cells located within defined regions of the nasal membrane. Thus, even if the toxin fragments are accidentally dispersed beyond the desired target regions, the fragments will not generally enter cells without the additional application of cell permeablizing or porating energy. For that reason, toxin delivery methods are particularly safe when performed with toxin fragments, such as the light chain of botulinum and other toxins.

While the remaining portion of this disclosure will be presented with specific reference to the botulinum toxin, one of skill in the art will appreciate that other toxins may also be used, including the active fragment of the toxin in combination with energy-mediated delivery protocols. Additionally, other therapeutic agents may also be used, including those that are non-toxic.

Figure 1:
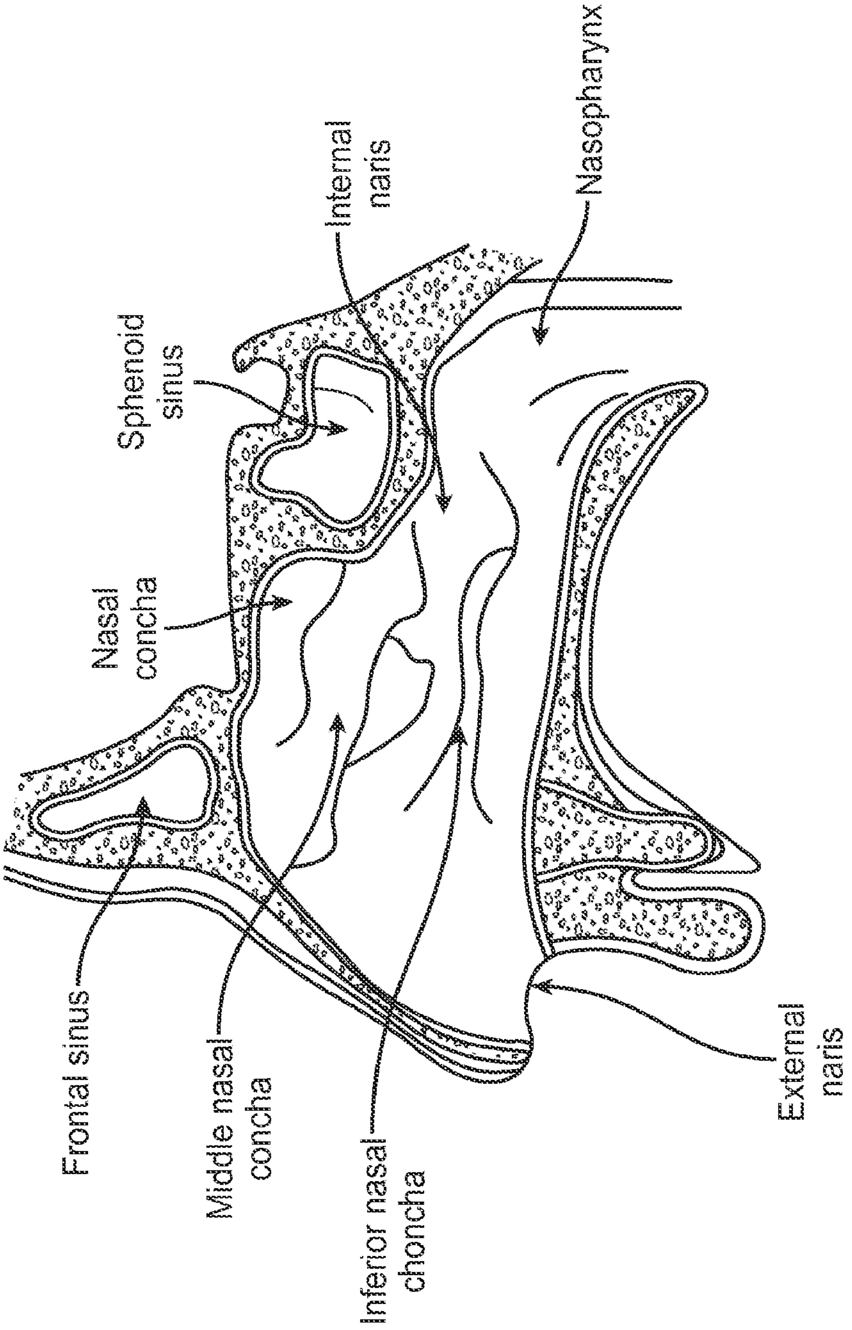
FIG. 1 illustrates basic anatomy of the nasal cavity.

FIG. 1 illustrates the basic anatomy of the nasal cavity. The entrance to the nasal cavity is via the external naris. Long, narrow, and curled bone shelves line a portion of the nasal cavity. These bones are referred to as nasal concha or turbinates. An upper or superior turbinate, a middle turbinate, and an inferior turbinate divide the nasal airway into four channel-like air passages which direct inhaled air to flow in a steady, regular pattern around the largest possible surface of cilia and climate controlling tissue. Various sinus cavities are also disposed within the bones of the face and skull adjacent the nasal cavity. These sinuses, such as the frontal sinus and the sphenoid sinus are mucosa lined airspaces that produce mucus. The nasal cavity communicates with the throat via the nasopharynx.

Figure 2:
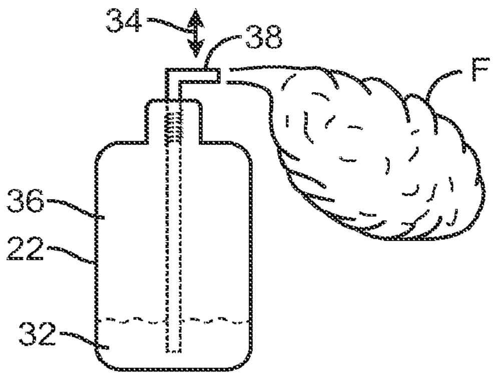
FIG. 2 illustrates a pump dispenser for generating foam.

FIG. 2 illustrates a pump dispenser 22. The dispenser 22 includes a container 36 holding a mixture 32 of a liquid, the therapeutic agent, and preferably a surfactant. Actuation 34 of the pump dispenser 22 causes air bubbles to become entrapped in the liquid, preferably an aqueous solution such as water or saline. The surfactant reduces surface tension of the liquid, thereby further enhancing entrapment of the gaseous bubbles in the liquid, resulting in the creation of foam F which is discharged from a nozzle 38 or elongate shaft connected to the pump dispenser 22. The foam expands in volume as it is discharged from the nozzle 38, and carries the therapeutic agent.

Figure 3:
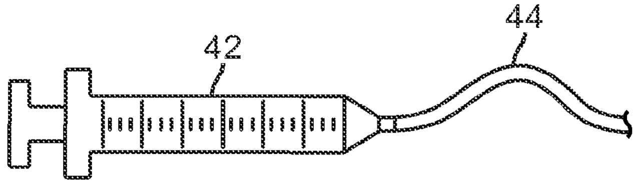
FIG. 3 illustrates a syringe for delivering foam.
Figure 4:
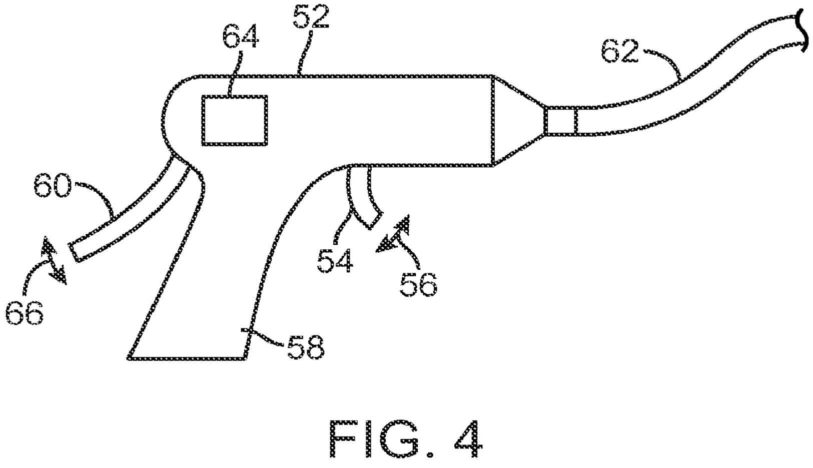
FIG. 4 illustrates a combined foam generating and pumping gun.

The foam may be manually transferred to the target treatment area, or the foam may be pumped directly from the dispenser 22 to the treatment area. FIG. 3 illustrates a syringe 42 which may also be used to deliver the foam to a target area. A flexible tube 44 coupled to the syringe 42 may also be used to access tight spaces and help direct the foam from the syringe to the target treatment area. FIG. 4 illustrates an exemplary embodiment of a combined foam generating mechanism and pump that can be used to form the foam and deliver it. The generating and pumping apparatus 52 includes a reservoir 64 holding the reagents such as a liquid, surfactant, and therapeutic agent. Actuation 56 of a primary pump mechanism 54 forms the foam similar to the dispenser 22 described above, and actuation 66 of a secondary pump mechanism 60 delivers the foam through an optional flexible tube 62 to the target site. The apparatus 52 includes a pistol grip 58 ergonomically designed for ease of grasping by the operator's hand.

One of skill in the art will appreciate that many other systems for generating foam may be used. In addition to pump dispensers as described above, the foam generation device may be constructed similarly to nitrous oxide cartridge based whipped cream dispensers, industrial foamers such as those available from Now Engineering (House Springs, Mo.), pest control foamers from Rockwell Labs (N. Kansas City, Mo.), cleaning foamers from Sun Brite Supply (Lawrenceville, Ga.), pesticide sprayers from ePetsupply.com (Dallas, Tex.), car wash foamers, or shaving cream foamers.

FIGS. 5A-5H illustrate an exemplary method of using foam to deliver a toxin to the nasal cavity. A toxin such as botulinum toxin is contained in the pump dispenser 22 along with a liquid such as water or saline and preferably a surfactant. The pump dispenser 22 is constructed as described above. Thus, actuation of pump dispenser 22 will force air bubbles into the liquid thereby forming a foam which is pumped out of the dispenser nozzle. The nozzle (not visible) is typically an elongate arm or shaft extending laterally outward from the pump dispenser. The nozzle may be used to help direct the foam into the nasal cavity or other target area. The surfactant reduces surface tension of the liquid facilitating formation of foam, and actuation of the pump dispenser 22 also disperses the toxin in the foam. One of skill in the art will appreciate that any of the liquids, toxins, surfactants, and anti-foaming agents disclosed in this specification may be substituted or combined with one another to produce the foam. Additionally, one of skill in the art will also appreciate that other liquids and reagents and mechanisms may also be used to generate the foam. Additionally, any of the foam delivery devices disclosed herein may be used to deliver the foam into the nasal cavity.

Figure 5A:
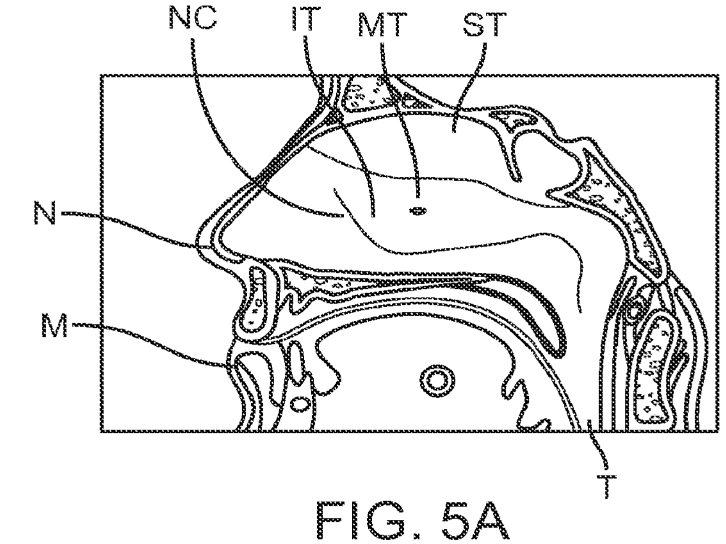
FIGS. 5A-5H illustrate an exemplary method of using foam to deliver a toxin to the nasal cavity.

FIG. 5A is a cross-sectional model of the nasal cavity NC with a translucent top surface to allow the interior of the nose to be seen. The model includes the mouth M, nose N, nasal cavity NC, turbinates, and throat T. The three turbinates include the superior turbinate ST, middle turbinate MT, and inferior turbinate IT.

Figure 5B:
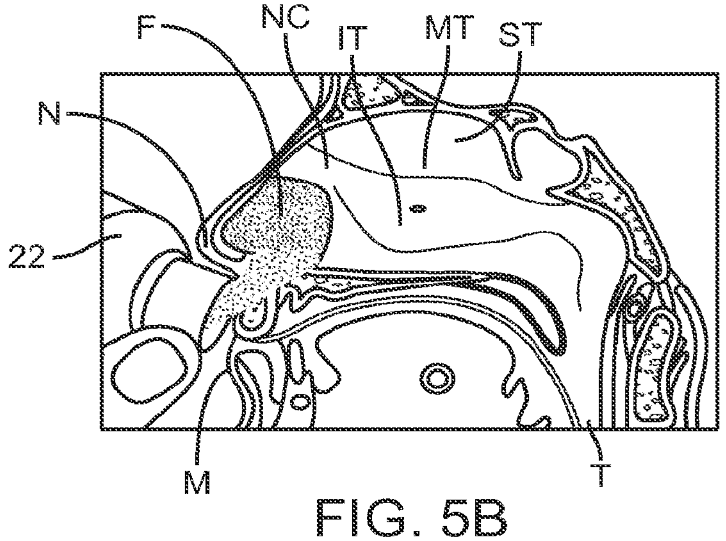
Figure 5C:
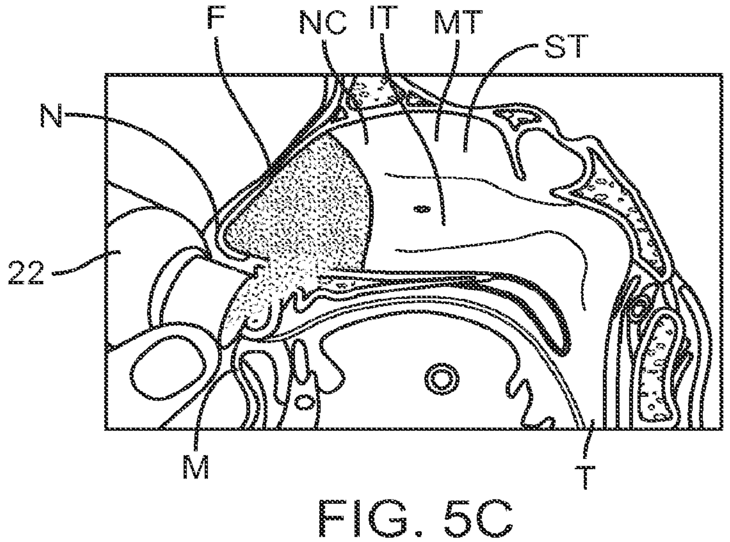
Figure 5D:
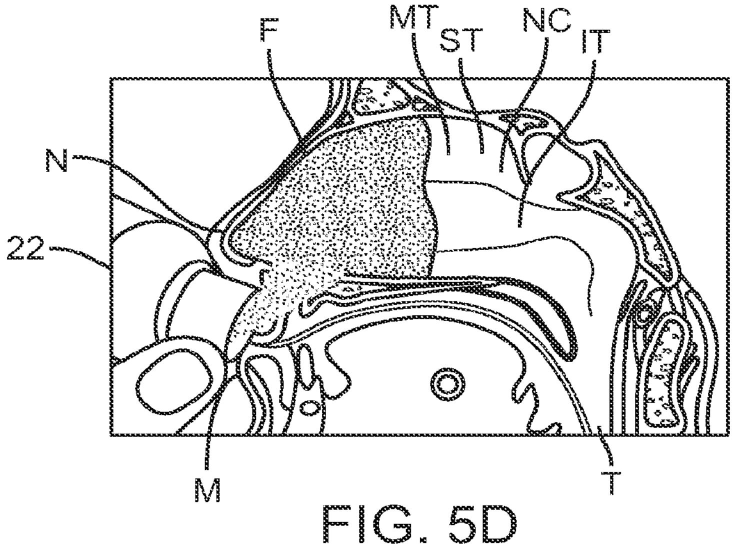
Figure 5E:
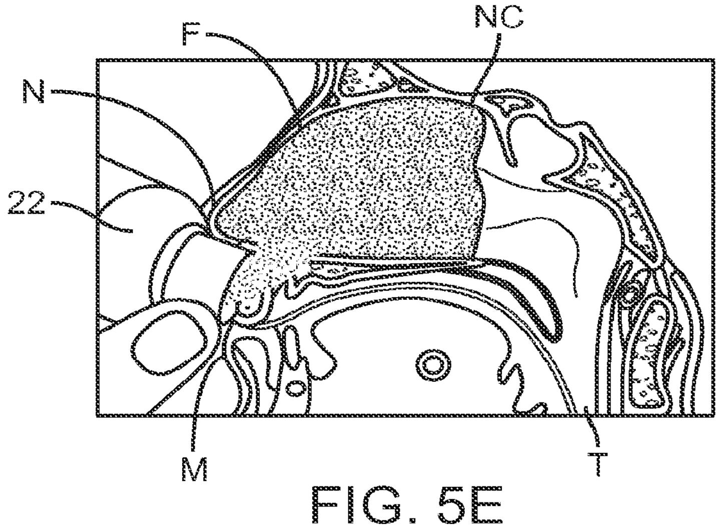
Figure 5F:
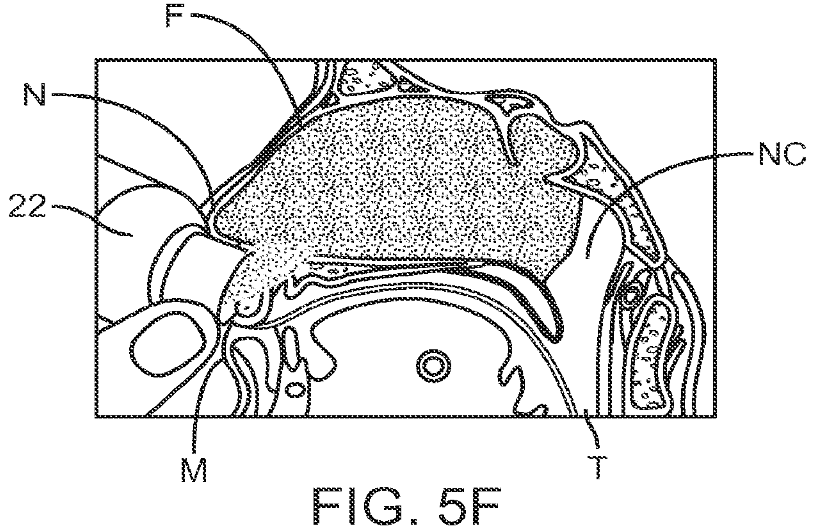
Figure 5G:
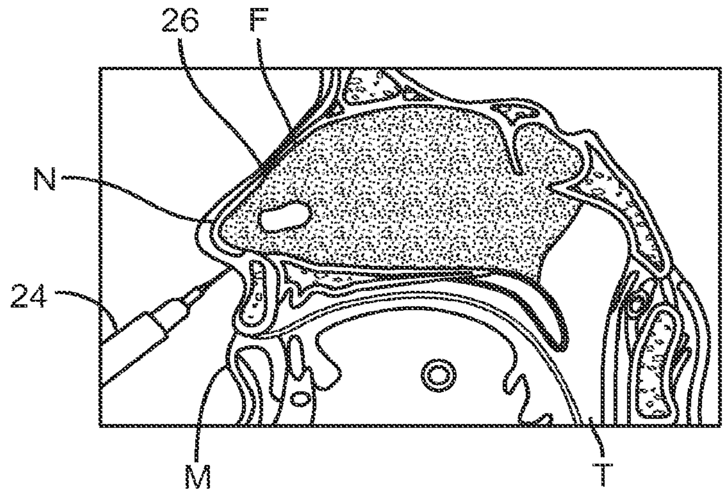

In FIG. 5B a pump dispenser 22 is advanced so that its nozzle is in engagement with a nostril of the nose N. A first actuation of the pump dispenser 22 forces foam F containing the toxin into the nasal cavity NC. A second actuation of the pump dispenser 22 forces additional foam F into the nasal cavity NC as seen in FIG. 5C. A third, fourth, and fifth actuation of the pump dispenser 22 continue to deliver foam F into the nasal cavity as seen in FIGS. 5D-5F, until the nasal cavity is substantially filled with foam as seen in FIG. 5F. Continued introduction of foam into the nasal cavity can also direct foam into the sinuses via various ducts and apertures in the nasal wall. While the nasal cavity NC is substantially filled with foam, it is not overfilled with foam F so as to avoid the passage of foam F through the nasopharynx into the esophagus or trachea, so that the therapeutic agent contained therein is not delivered to an undesired location such as the lungs. The foam is permitted to reside in the nasal cavity for a predetermined time in order to allow the therapeutic agent that is dispersed therein to be delivered into the mucosa. In this exemplary embodiment, the therapeutic agent is a toxin such as botulinum toxin which will inhibit mucus secretions.

The delivery means might also plug the nostril, to prevent the inadvertent inhalation of the foam. The plug will keep the foam in the nasal passage for the desired time, at which point the plug can be removed.

The foam might also be designed to disintegrate into a thick sticky coating on the surface of the mucous membranes containing a high concentration of toxin in a small volume of coating.

Figure 5H:
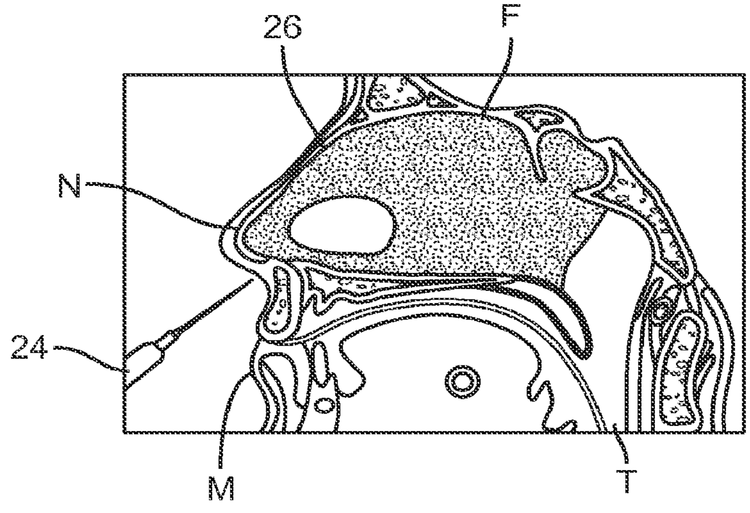

After the foam F has resided in the nasal cavity for a sufficient time to allow an effective amount of the therapeutic agent to be delivered to the mucosa, the foam is removed from the nasal cavity, preferably by aspiration. Optionally, an anti-foaming agent such as simethicone may be delivered via a syringe 24 placed in a nostril of the nose N. The anti-foaming agent helps facilitate removal of the foam by reducing the foam from its expanded configuration into a watery, collapsed configuration that is easier to aspirate. The simethicone immediately begins to reduce the foam from its expanded configuration to its collapsed watery configuration as seen by void 26 in FIG. 5G. Other possible anti-foaming agents include silicone oils, polyethylene glycol, polypropylene glycol copolymers, and dishwasher detergents. After a sufficient amount of the anti-foaming agent is delivered to the nasal cavity NC, the syringe 24 is removed from the nose, and the foam F continues to collapse, as seen in FIG. 5H by the larger void 26. After the foam has collapsed, it may be aspirated out with a suction wand, syringe, or other instrument. The anti-foaming agent might also accelerate the collapse of the foam into a sticky layer which remains on the mucous membranes for an extended period.

While the exemplary embodiment above describes substantially filling the nasal cavity with the foam and toxin, the amount of foam may be controlled so that only a portion of the cavity is filled. Additionally, because the foam consistency can be controlled, the foam can support its own weight and remain in a desired position. Thus, foam may be delivered to a specific target location within the nose. For example, the foam may be delivered and fill only a posterior portion of the nasal cavity, or only an anterior portion of the cavity may be filled with foam. In still other embodiments, the foam may be directed to the various channels formed by the turbinates. Thus foam may be delivered to the channel superior to the superior turbinate, or to the channel between the superior and middle turbinate. Foam may also be selectively delivered to the channel between the middle and inferior turbinates, or to the channel inferior to the inferior turbinate. In still other embodiments, the foam may be delivered to any combination of the channels defined by the turbinates.

Foam properties such as expansion volume and longevity can be controlled by varying the reagents used to form the foam, as well as their ratios and the methods used to force the gaseous bubbles into the liquid. Several experiments were conducted and are summarized below to test some of these variables.

Experiment 1. A 0.9% sodium chloride USP aqueous solution was combined with a surfactant. Surfactants included liquid off the shelf soaps, sodium dodecyl sulfate (SDS) or Polysorbate 20 (also known as Tween). The liquid soaps contained water, vegetable oils (such as coconut, castor, soybean, apricot kernel, sunflower seed, meadow flower seed, and shea butter), and potassium hydroxide. Various ratios of saline to surfactant were used. A 3:1 ratio of saline to surfactant easily generated foam when passed through a foam generating mechanism. The foam generating mechanism included a pump dispenser similar to a hand soap pump or a whipped cream canister with nitrous oxide cartridges. A 6:1 ratio also produced foam, but the foam had shorter longevity than the foam formed with a 3:1 ratio of saline to surfactant. Using the 3:1 ratio with a pump bottle containing saline, and either soap, SDS, or Tween produced foams of similar appearance. The foams were white, with a distribution of small uniform bubbles and remained self supporting for at least 15 minutes.

In addition to using the pump dispenser, other mechanical methods were used to introduce the gaseous bubbles into the saline such as by manually shaking the mixture in a container or using a whipped cream canister with nitrous oxide cartridges. The manual agitation forms a weak foam with large bubbles that only lasted for 1-2 minutes. The nitrous oxide canister method also generated a white foam, but the foam rapidly subsided into a pool of liquid.

Experiment 2. A 3:1 saline-soap mixture was placed in a pump dispenser. Actuating the pump produced a volume of foam that was approximately ten times the liquid volume. The foam subsided slowly over time, but even after 15 minutes the foam retained most of its original volume. A container was filled with 120 ml of the foam. One milliliter of simethicone anti-foaming agent was added to the foam which then subsided rapidly into a collapsed liquid configuration. The remaining liquid volume was about 12.5 ml, and thus the foam volume was more than ten times the liquid volume. In contrast, a 6:1 saline-soap foam mixture formed with a nitrous oxide canister produced 90 ml of foam that resolved quickly into 18 ml of liquid. Thus, the 6:1 ratio produced foam having a 5× expansion factor. A similar expansion factor was observed when using a 3:1 ratio of saline-soap with the nitrous oxide canister.

The nasal volume of the first 5.2 cm of the nasal passage has been estimated by Kjoergaard to be about 5.43 $cm^3$±1.31 $cm^3$ per side based on acoustic rhinometry. Topical application of toxins to the nasal cavity have been reported by Rohrbach to use a sponge filled with 40 U (per side) with a concentration of 25 U/ml of toxin. Delivering the same 40 U dose to the nasal cavity with foam having a 10× expansion factor would require approximately 0.5 ml of an 80 U/ml liquid drug solution.

Experiment 3. Volunteers evaluated the sensation of various 3:1 mixtures of foam after the foam was delivered to their nasal cavities. In some instances, the pump dispenser was used to deliver the foam directly to the nostril, while in other cases the pump was used to generate the foam and then the foam was transferred to a syringe for delivery to the nasal passage. The test subjects reported that soap and SDS had a mild stinging sensation in their nose, while Tween did not sting. However, foam produced with Tween did drip out of the nostril after a few minutes, and was easily stopped by pinching the nostril. Use of simethicone as an anti-foaming agent did result in sneezing and a sensation of post nasal drip.

The 3:1 solution of saline and Tween appears to be a promising mixture for producing foam that remains self supporting for at least 15 minutes and is not associated with any unpleasant sensations in the nose.

In addition to using foam to deliver a therapeutic agent to the nasal cavity, slurries may also be used. A slurry is a thick suspension of solids in a liquid. The solids take up space in the slurry, thereby expanding the slurry volume. The therapeutic agent, such as a toxin can be added to the slurry which is then delivered to the nose. Because viscosity of the slurry can be controlled to have a desired thickness, the slurry will fill the nasal cavity space and not run to undesired locations. The solid particles in the slurry may be porous if desired, but preferably the solids would have a pore size smaller than the molecule size of the therapeutic agent or toxin, to ensure that the drug is delivered to the tissue, and not absorbed into the slurry solids. One exemplary embodiment of a slurry also contains cross-linked gelatin particles. After the slurry has been delivered to the target site, thrombin in the slurry causes expansion of the slurry for maximum tissue contact.

In another embodiment, the solution of Botox can be added to hydrogel particles such that the amount of liquid in the system is equal to or less than the equilibrium water content of the hydrogel. In this way, the particles will contain the Botox, but there will not be any free liquid that could be problematic. The Botox will still be able to reach the target tissue by diffusion from the hydrogel particles. After remaining in place for a period of time, the particles can be flushed from the nasal cavity via a canula. In a more specific embodiment, hydrogel particles contain an active ingredient at less than the equilibrium water content of the hydrogel, such as FloSeal Matrix from Baxter, in which case the hydrogel is crosslinked gelatin and the active ingredient is thrombin.

Particles for use in the slurry may include polyvinylpyrrolidone (PVP) which is a light flaky powder when dry. PVP is soluble in water, and readily absorbs up to 40% of its weight in atmospheric water. In solution it has excellent wetting properties and readily forms films. This makes it good as a coating or an additive to a coating. It is commonly used as a binder in pharmaceutical tablets, as a thickening agent, an adhesive, an emulsifier, and is commonly used as Betadine to sterilize surgical fields.

Hemostatic products may be chopped up and shredded and added to the slurry to expand it's volume and control viscosity. For example, Surgicel (an Ethicon product) includes an oxidized cellulose polymer. It is commonly used in ear, nose, and throat (ENT) procedures. Oxycel (Becton Dickenson) also has an oxidized cellulose polymer, but uses hollow fibers. Avitene (Davol) is a powder form of bovine collagen or a collagen sponge that may be used in the slurry. Gelfoam Plus (Baxter Healthcare) is packaged as a gelfoam sponge and includes purified porcine skin and gelatin particles, along with thrombin powder and sterile saline. This product swells during use, which may be a benefit in the nasal cavity. Spongostan (Ethicon) is an absorbable porcine gelatin sponge which liquefies in 2-5 days when applied to bleeding mucosal surfaces, and is absorbed in 4-6 weeks. Floseal hemostasis matrix (Baxter Healthcare) consists of bovine derived gelatin granules coated in human derived thrombin.

Figure 6:
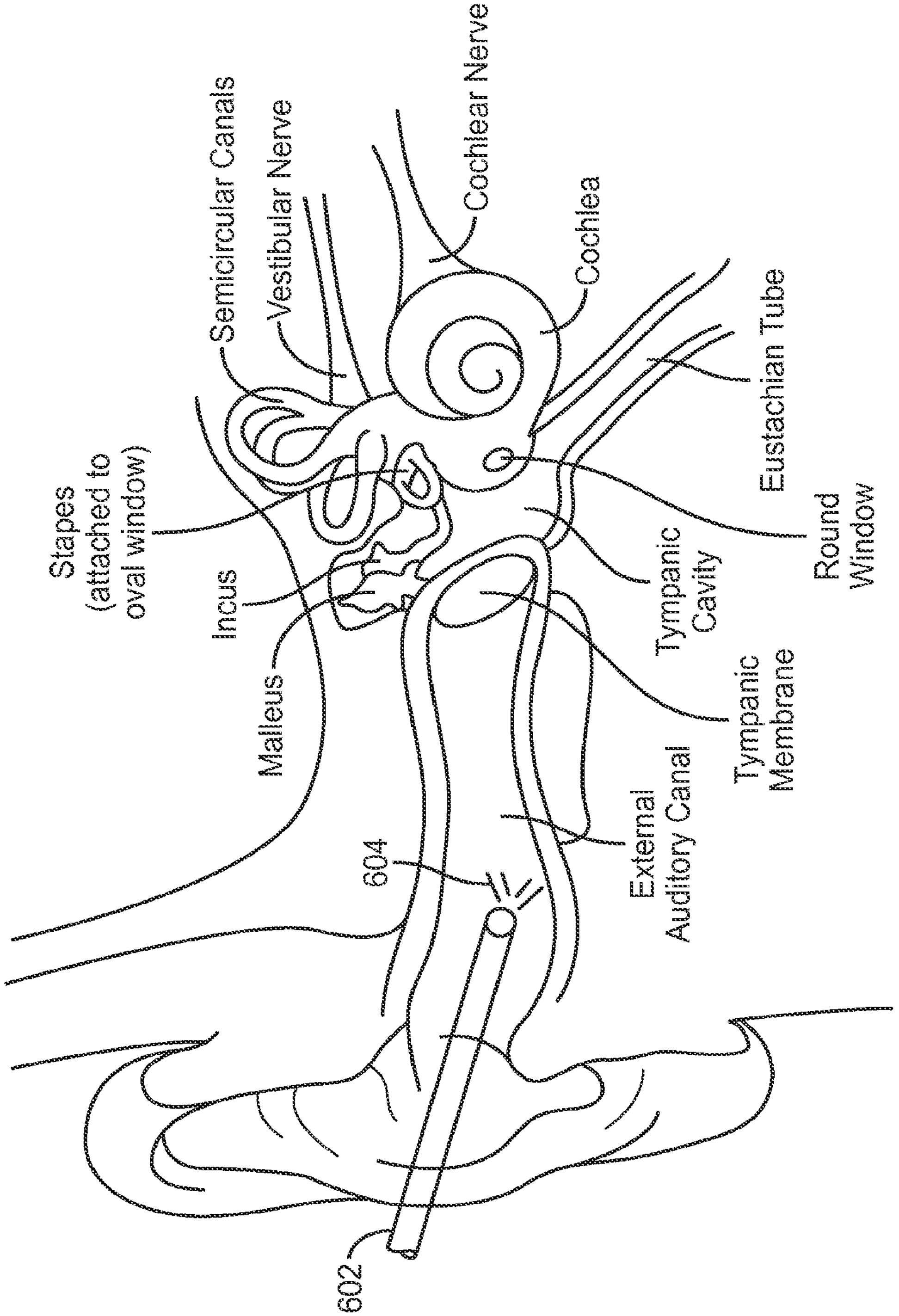
FIG. 6 illustrates an exemplary method of using foam to deliver a therapeutic agent to the ear.

In alternative embodiments, foam may be used to deliver therapeutic agents to other body cavities to treat target tissues such as mucous membranes or other target tissues therein. For example, therapeutic agents maybe delivered in a foam configuration to the vagina, rectum, bladder, urethra, ear, etc. In an exemplary embodiment, a therapeutic agent such as an antibiotic may be delivered in foam form into the ear canal as a treatment for ear infections. In another exemplary embodiment, a therapeutic agent may be delivered via the urethra to the bladder as a treatment for an overreactive bladder. The therapeutic agent may be a toxin, an antibiotic, or any other medicament. FIG. 6 illustrates an exemplary embodiment where a elongated shaft 602 such as a catheter or other flexible tube is inserted into the external auditory canal. The elongated shaft 602 may be coupled to a pump or reservoir (not illustrated) so that foam 604 can be delivered through the elongated shaft 602 into the ear. A therapeutic agent may be dispersed in the foam. The foam may fill all or only a portion of the canal, or the foam may fill portions of the inner ear. Exemplary therapeutic agents include antibiotics for treatment of ear infections. One of skill in the art will appreciate that other therapeutic agents may also be used to treat other conditions.

Figure 7:
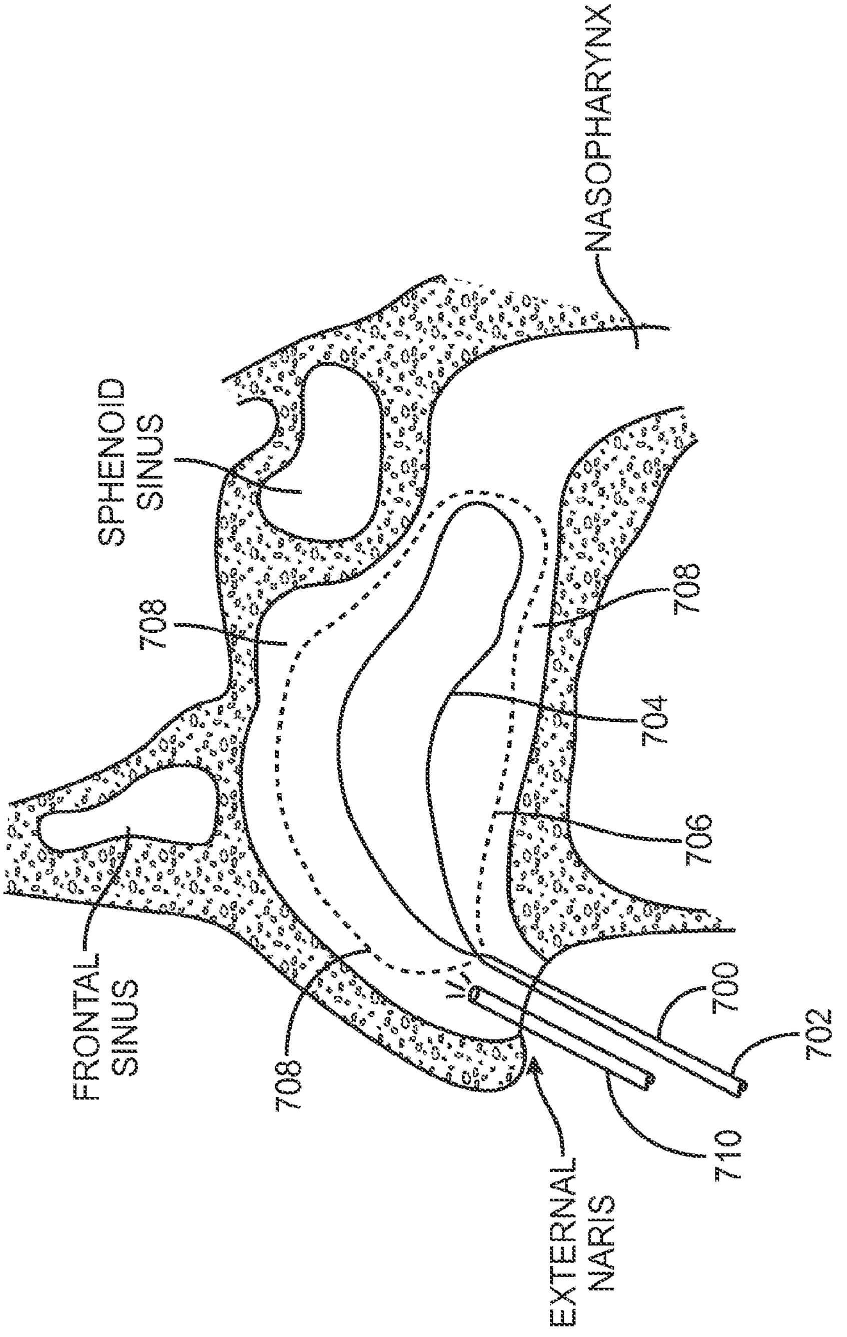
FIG. 7 illustrates the use of an expandable member with a foam dispenser.

FIG. 7 illustrates the use of an expandable member with a foam or slurry dispenser. The expandable member 700 includes an elongate shaft 702 having an expandable member 704 adjacent a distal portion of the elongate shaft 702. The expandable member 704 may be a balloon or other volume filling member that has a collapsed configuration and an expanded configuration. The collapsed configuration is adapted to allow the elongate shaft and expandable member to be inserted and correctly positioned into a nasal cavity or other body cavity. The expanded configuration may be adapted to substantially fill most of the cavity while leaving a small space 708 between an outer surface of the expandable member and the walls of the cavity. The expandable configuration is indicated by the expandable member in phantom in FIG. 7. This small space may be filled with the foam, slurry, or therapeutic agent from a dispenser 710. The dispenser 710 may be any of the dispensers disclosed herein. The expandable member allows the foam or slurry with the therapeutic agent to be delivered to the desired target while minimizing the volume required to fill the space. The expandable member may expand to a shape similar to that of the cavity so that a space is left all around the expandable member, or the expandable member may expand and contact the cavity walls to prevent the foam and therapeutic agent from contacting portions of the cavity, thus allowing targeting of some regions and avoidance of other regions. In alternative embodiments, the expandable member may remain compressible when fully expanded into engagement with the cavity walls and the foam may be injected under pressure to force its way between the expandable member and cavity wall.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for delivering a therapeutic agent to a nasopharyngeal mucosa target, said method comprising:

entrapping gaseous bubbles in a liquid thereby forming a liquid foam;

dispersing a therapeutic agent in at least one of the liquid or the liquid foam, wherein the therapeutic agent comprises a neurotoxin;

delivering the liquid foam to a nasopharyngeal space so that the therapeutic agent is delivered to the mucosa target, wherein the foam has a distribution of entrapped gas bubbles so as to be self-supporting within the nasopharyngeal space;

inserting an instrument into the nasopharyngeal space; and removing the liquid foam from the nasopharyngeal space with the instrument before the liquid foam disintegrates completely.

2. The method of claim 1, wherein entrapping gaseous bubbles in the liquid comprises actuating a foam generating mechanism.

3. The method of claim 2, wherein the foam generating mechanism comprises a pump.

4. The method of claim 2, wherein the foam generating mechanism comprises a pressurized container wherein the gas is passed into the liquid.

5. The method of claim 2, wherein the foam generating mechanism comprises a container holding the gas, the liquid, and the therapeutic agent, the method further comprising agitating the container or its contents to mix the contents therein thereby forming the liquid foam with the therapeutic agent dispersed therein.

6. The method of claim 1, wherein the gaseous bubbles comprise air.

7. The method of claim 1, wherein the gaseous bubbles comprises nitrous oxide.

8. The method of claim 1, wherein the liquid comprises an aqueous solution.

9. The method of claim 1, wherein the liquid comprises saline.

10. The method of claim 1, wherein entrapping the gaseous bubbles further comprises adding a surfactant to the liquid thereby lowering surface tension between the bubbles and the liquid so as to facilitate formation of the liquid foam.

11. The method of claim 10, wherein the surfactant comprises soap, sodium dodecyl sulfate, or a polysorbate surfactant.

12. The method of claim 1, wherein the neurotoxin is configured to inhibit mucus secretions.

13. The method of claim 1, wherein the neurotoxin comprises botulinum toxin.

14. The method of claim 1, wherein delivering the liquid foam comprises substantially filling up the nasopharyngeal space with the liquid foam.

15. The method of claim 1, wherein inserting the instrument comprises advancing an elongate shaft into the nasopharyngeal space and passing the liquid foam therethrough to the mucosa target.

16. The method of claim 1, wherein delivering the liquid foam comprises passing the foam through a syringe.

17. The method of claim 1, further comprising retaining the liquid foam in the nasopharyngeal space for a time period long enough for an effective amount of the therapeutic agent to be absorbed by the mucosa target.

18. The method of claim 1, wherein delivering the liquid foam comprises actuating a pump mechanism.

19. The method of claim 1, wherein removing the liquid foam comprises aspirating the liquid foam from the nasopharyngeal space.

20. The method of claim 1, wherein removing the liquid foam comprises adding an anti-foaming agent to the liquid foam thereby breaking the liquid foam down into a reduced volume configuration for removal from the nasopharyngeal space.

21. The method of claim 20, wherein removal of the liquid foam in a reduced volume comprises expulsion from the nasopharyngeal space by nose blowing by the patient.

22. The method of claim 20, wherein the anti-foaming agent comprises one of simethicone, silicone oil, polyethylene glycol, polypropylene glycol copolymer, and detergent.

23. The method of claim 1, wherein the therapeutic agent alleviates symptoms associated with rhinitis.

24. The method of claim 1, further comprising expanding an expandable member in the nasopharyngeal space while maintaining a space between an outer surface of the expandable member and a wall of the nasopharyngeal space, wherein the liquid foam is delivered to the space between the outer surface of the expandable member and the wall of the nasopharyngeal space.

* * * * *